United States Patent [19]

Duff

[11] Patent Number: 4,948,883

[45] Date of Patent: Aug. 14, 1990

[54] PREPARATION OF HYDROGEN AND BISMUTH (PHOSPH/SULF) ATED SACCHARIDES

[75] Inventor: Steven R. Duff, DeSoto, Kans.

[73] Assignee: Marion Laboratories, Inc., Kansas, Mo.

[21] Appl. No.: 430,059

[22] Filed: Oct. 31, 1989

Related U.S. Application Data

[63] Continuation-in-part of Ser. No. 351,714, May 15, 1989, abandoned.

[51] Int. Cl.$^5$ ................. C07H 11/00; C07H 13/00; C07H 1/00; C08B 37/00
[52] U.S. Cl. .................. 536/117; 536/17.1; 536/118; 536/121; 536/124; 536/122
[58] Field of Search ............. 536/117, 17.1, 121, 536/124, 122, 118

[56] References Cited

U.S. PATENT DOCUMENTS 3,379,717  4/1968  Koopman et al. ............. 536/18.1
3,432,489  3/1969  Nitta et al. ................. 536/118

FOREIGN PATENT DOCUMENTS 0230023  7/1987  European Pat. Off. .

OTHER PUBLICATIONS

Andersen et al., (Eds.), *Chem Sources U.S.A.*, pp. 158, 257, 259, 311, 326, 447 and 467, Directories Publishing Co., Inc., Ormond Beach, FL (1984).
Carey et al., *Advanced Organic Chemistry, Part B: Reactions and Synthesis*, Plenum Press, New York (1977), pp. 482–496 and 507.
Bowen et al., U.S. Ser. No. 07/209,372 filed on Jun. 21, 1988.

*Primary Examiner*—Ronald W. Griffin
*Assistant Examiner*—Everett White
*Attorney, Agent, or Firm*—Christopher J. Rudy

[57] ABSTRACT

Bismuth salts of phosphorylated and/or sulfonated saccharides are prepared from a corresponding metal salt reactant, a water soluble organic acid, and a bismuth substance. For example, a complex salt of bismuth hydroxide sucrose octasulfate can be prepared in high yield and good purity from potassium sucrose octasulfate, trichloroacetic acid, trifluoroacetic acid or 4-methylbenzenesulfonic acid, and bismuth hydroxide. Corresponding hydrogen phosphorylated and/or sulfonated saccharides may be intermediate products.

10 Claims, No Drawings

PREPARATION OF HYDROGEN AND BISMUTH (PHOSPH/SULF) ATED SACCHARIDES

This is a continuation-in-part of application Ser. No. 07/351,714, filed 05/15/89, incorporated herein by reference, abandoned.

FIELD

This invention especially concerns preparation of hydrogen and bismuth phosphorylated and/or sulfonated saccharides. These saccharides are generally useful as pharmaceuticals or intermediates thereto.

BACKGROUND

Various hydrogenn (phosph/sulf)ated saccharides are known. See, Andersen et al. (Eds.), *Chem Sources U.S.A.*, Directories Publishing Co., Inc., Ormond Beach, Fla. (1984), pages 158, 257, 259, 262, 311, 326, 447 & 467, for some examples of those commercially available.

Bowen et al., U.S. patent application Ser. No. 07/209,372 filed on Jun. 21, 1988, U.S. Pat. No. 4,918,175 (Apr. 17, 1990), discloses bismuth (phosph/sulf)ated saccharides. In nature and gist, these compositions are bismuth phosphorylated and/or sulfonated saccharides, which are useful as pharmaceuticals in ameliorating disorders associated with gastric mucosal damage. Preparation of the bismuth (phosph-sulf)ated saccharides according to the practice of that invention involves contacting a hydrogen (phosph/sulf)ated saccharide with a bismuth substance. Preparations from metal salts of the (phosph/sulf)ated saccharides, other than bismuth of course, involve, for example, ion exchange procedures with an ion exchange resin such as a sulfonated divinyl benzene in its hydrogen ion form. The metal salt, for example, the potassium salt, is passed over the resin to prepare the hydrogen (phosph/sulf)ated saccharides, which are used for contacting with the bismuth substance, for example, freshly prepared bismuth hydroxide, to prepare the bismuth (phosph/sulf)ated saccharides.

What is lacking and needed is a process which can prepare hydrogen and/or bismuth (phosph/sulf)ated saccharides, particularly from salts other than of course bismuth, that is simpler and more efficient thhan heretofore known. Desirably, the process would be employable with advantage in preparation of large or commercial scale amounts of the product (phosph/sulf)ated saccharide.

SUMMARY

This invention, in one aspect, provides a process for preparing a hydrogen (phosph/sulf)ated saccharide comprising contacting a metal salt of a (phosph/sulf)ated saccharide with a water soluble organic acid having a pKa less than the pKa of the hydrogen (phosph/sulf)ated saccharide to be prepared, by steps under conditions such that the hydrogen (phosph/sulf)ated saccharide is prepared. Another aspect provides a process for preparing a bismuth (phosph/sulf)ated saccharide comprising steps of contacting, first, a metal salt of a (phosph/sulf)ated saccharide with a water soluble orgnaic acid having a pKa less than the pKa of a hydrogen (phosph/sulf)ated corresponding to the bismuth (phosph/sulf)ated saccharide to be prepared, and second, the product of said first step with a bismuth substance, by steps under conditions such that the bismuth (phosph-sulf)ated saccharide is prepared.

This invention is useful for preparing pharmaceutical intermediates and/or products.

This invention fulfils the aforementioned lacks and needs in the art. Advantageously, this invention can be employed in highly efficient preparation of large or commercial scale amounts of the desired hydrogen and/or especially bismuth (phosph/sulf)ated saccharide(s) suitable as is as a pharmaceutically employable component.

Further significant advantages attend this invention.

ILLUSTRATIVE DETAIL

In general, the hydrogen and/or bismuth (phosph/sulf)ated saccharides prepared by the practice of this invention are those found in the art or from the practice of the mentioned Bowen et al. invention, which thus contain such a component as hydrogen or bismuth, respectively, and of which a full description follows herein. The (phosph/sulf)ated saccharides further contain suuch a component as a phosphorylated and/or a sulfonated saccharide, which is a saccharide generally having more than one moiety selected from such moieties as at least one of phosphate and sulfate moieties esterified thereto.

The component such as a sulfate ester and/or a phosphate ester saccharide includes thus such saccharides as (1) sulfated saccharides, (2) phosphated saccharides, (3) sulfated-phosphated saccharides, and (4) mixtures thereof. Saccharide components having at least three sulfate ester moieties per saccharide nucleus are desirablyy employed. Polysulfated saccharides are more typically employed in the practice of this invention. The polysulfated saccharides desirably contain substantial amounts of persulfated saccharides.

Saccharide moieties themselves which may be employed in the practice of this invention include mono-, di-, tri-, tetra- and oligosaccharides. Examples of suitable saccharide nuclei or moieties may be selected from appropriate residues of such saccharides as erythrose, threose, arabinose, deoxyribose, fructose, glucose, ribose, mannose, lactose, cellobiose, maltose, sucrose, trehalose, melezitose, stachyose, and so forth and the like. The saccharide moieties desirably are disaccharides of pentoses and/or hexoses. Sucrose is preferred.

In general, the bismuth (phosph/sulf)ated saccharides contain the component such as bismuth. The component such as bismuth includes such metallic elements as bismuth, and especially in the final pharmaceutical product, pharmaceutically acceptable compounds therewith.

Pharmaceutically acceptable compounds with bismuth include, of course, molecular level covalent or ionic complexes with bismuth and the phosphated and/or sulfated saccharide moieties, molecular level covalent or ionic complexes with such bismuth-containing moieties or compounds as bismuth hydroxides and the phosphated and/or sulfated saccharide moieties, these compositions in the presence of a suitable pharmaceutical carrier, and so forth and the like.

The bismuth (phosph/sulf)ated saccharides may be a composite mixture, i.e., a composition combining more than one chemical entity to make up the composition. They may be considered complex bismuth salts of (phosph/sulf)ated saccharides(s).

The bismuth (phosph/sulf)ated saccharides are generally insoluble in water, lower alcohols, e.g., methanol, lower ketones, e.g., acetone, dilute aqueous hydrochloric acid, for example, 0.1N HCl(aq), with generally no gelling propensity in acidic water.

In general, the hydrogen (phosph/sulf)ated saccharides are saccharides analogous to those of the corresponding bismuth (phosph/sulf)ated saccharides, but having phosphoric and sulfonic acid moieties bonded therewith. Sulfonic acids are preferred.

The hydrogen (phosph/sulf)ated saccharides are generally soluble in water and such hydroxylated organic compounds as methanol, ethanol, propanols, and so forth. Preferably, the hydrogen (phosph/sulf)ated saccharide is substantially soluble in a diluent in which the corresponding bismuth (phosph-sulf)ated saccharide is substantially insoluble in, advantageously, for example, water.

In general, the metal salts of the (phosph/sulf)ated saccharide employed in the practice of this invention are saccharides analogous to the hydrogen (phosph/sulf)ated saccharides but having metal ions generally replacing the hydrogen ions from phosphoric and sulfonic moieties of the hydrogen (phosph/sulf)ated saccharides. Suitable metals in this connection include alkali and alkaline earth metals, especially the alkali metals. Potassium salts are preferred.

Desired metal salts of the (phosph/sulf)ated saccharides are those being generally soluble in the same diluents as the hydrogen (phosph/sulf)ated saccharides are soluble, yet being substantially soluble in those diluents in which the corresponding bismuth (phosph-sulf)ated saccharides are substantially insoluble. Advantageously, such a diluent is one as, for example, water.

Phosphorylation and/or sulfonation may be accomplished on corresponding saccharides having appropriate esterfication site(s) available, as is known in the art. For example, phosphorylation may be accomplished by appropriate treatment of a hydrogen saccharide with a suitable phosphorylating agent, for example, one which may be phosphoryl chloride or cyanoethyl phosphate. See e.g., Carey et al., *Advanced Organic Chemistry, Part B: Reactions and Synthesis*, Plenum Press, New York (1977), at pages 482-96 & 507. Sulfonation may be accomplished by appropriate treatment of a hydrogen sacchride with a suitable sulfating agent, for example, chlorosulfonic acid, anhydrous sulfuric acid or sulfur trixode-pyridine complex in a solvent such as pyridine, formamide, dimethyl formamide, chloroform or liquid sulfur dioxide. See e.g., Nitta et al., U.S. Pat. No. 3,432,489. See also, for example, Michaeli, EP 0,230,023, especially for preparations with and illustrations of sodium and potassium sulfate saccharides.

Such phosphorylation and/or sulfonation can be used at the end of the first major phase of the present invention with incompletely phosphorylated or sulfated saccharides to prepare more highly phosphorylated or sulfated saccharides, to include mixed varieties thereof, and then these products can be contacted with the bismuth substance as desired. Alternatively, known hydrogen (phosph/sulf)ated saccharides can be phosphorylated and/or silfonated. Such hydrogen (phosph/sulf)ated saccharides can be converted into a metal salt of the (phosph/sulf)ated saccharide for use as a reactant in the process of this invention if desired.

Thus, the metal salts of the (phosph/sulf)ated saccharides employed in the practice of the invention are known, or they can be prepared by known methods or methods analogous thereto. Many of the metal salts of the (phosph/sulf)ated saccharides employed in the practice of this invention can be obtained commercially.

In general, the water soluble organic acid having a pKa less than thhe pKa of the hydrogen (phosph/sulf)ated saccharide to be prepared or which corresponds to the bismuth (phosph/sulf)ated saccharide to be prepared has the following characteristics, among others. It is generally, advantageously—substantially, and preferably—completely, soluble in water or the reaction media in which it is employed in the practice of this invention. It is an organic acid, i.e., an acid bearing organic carbon, as this is known in the art. It has a pKa less than the pKa of the hydrogenn (phosph/sulf)ated saccharide to be prepared, or it has a pKa less than a hydrogen (phosph/sulf)ated saccharide appropriately corresponding to the bismuth (phosph/sulf)ated saccharide to be prepared, generally exclusive of derivatization, for example, derivatization to the saccharide moieties or nuclei, or residues thereof, which can be carried out subsequent to preparation of the bismuth (phosph/sulf)ated saccharide which correspond to the hydrogen (phosph/sulf)ated saccharide in the practice of this invention. As an illustrative example, an aqueous solution of hydrogen sucrose octasulfate, commonly known as sucrose octasulfate, has a pKa of about 1.33. Accordingly, the organic acid used in the practice of this invention to prepare the hydrogen sucrose octasulfate or bismuth sucrose octasulfate will have a pKa of less than about 1.33, to include for example, a pKa of about 1.30 or less. Preferably, the water soluble organic acid used in the practice of this invention is selected from among appropriate carboxylic or sulfonic acids. Suitable illustrative examples thus include trichloroacetic acid, trifluoroacetic acid and 4-methylbenzenesulfonic acid, and so forth and the like. Desirably, the organic acid used in the practice of this invention is trifluoroacetic acid.

In general, the bismuth substance contains bismuth, which, when contacted with the hydrogen (phosph/sulf)ated saccharide, can form the bismuth (phosph/sulf)ated saccharide. As an illustration, the bismuth substance may be bismuth hydroxide (bismuth trihydroxide). Freshly prepared bismuth hydroxide is preferred. Commercially available bismuth hydroxide may contain other bismuth species such as bismuth carbonate, and/or bismuth oxides, and so forth, and may not work as well as the freshly prepared bismuth hydroxide in the practice of this invention.

In the practice of this invention, metal salt(s) of the (phosph/sulf)ated saccharide(s) is(are) contacted with the water soluble organic acid(s) having a pKa less than the pKa of hydrogen (phosph/sulf)ated saccharide(s) to be prepared or which correspond(s) to bismuth (phosph/sulf)ated saccharide(s) to be prepared. Conditions are those sufficient to prepare the desired product.

In general, amounts of the water soluble organic acid employed in the practice of this invention are those suitable to obtain the desired product. Typically, in terms of molar equivalents of phosphorylated and/or sulfated moieties on the saccharide nuclei of the (phosph/sulf)ated saccharide moieties of the metal salt of the (phosph/sulf)ated saccharide reactant employed, in comparison to molar equivalents of acid with the water soluble organic acid employed, molar equivalent amounts of organic acid equivalents are about from a slightly less than stoichiometric amount to a moderate excess amount in comparison to molar equivalent amounts of the phosphorylated and/or sulfated moieties on the saccharide moieties provided with reactant metal salt, for advantageous production. Of course, if less amounts of the water soluble acid are employed, incomplete conversion of the entire metal salt reactant sample to desired product may result. The moderate excess amount includes molar equivalent amounts of acid of the water soluble organic acid or about two times as many as molar equivalent amounts of phosphorylated and/or sulfated moieties on the (phosph/sulf)ated saccharide residues of the metal salt reactant sample employed. In terms of ratios of acid equivalents to phosphorylated and/or sulfated moiety equivalents, ratios of about from 0.8:1 to 1:2.5 are included as generally and advantageously suitable, with the typical of such ratios being about from 0.9:1 to about 1:2, and with preferred ratios being about from 0.9:1 to about 1:1.5. In terms of more typically employed metal salt reactants having polysulfated saccharide moieties, and of course, poly(phosph/sulf)ated saccharide moieties as well, a molar excess of the water soluble organic acid is typically employed in relation to number of molar equivalents of metal salt of the (phosph/sulf)ated saccharide containing such poly(sulfated and/or phosphorylated) saccharide moieties. The excess referred to is typically a substantial excess of the water soluble organic acid employed in the practice of this invention. The substantial excess include molar excesses of the organic acid at least about three times the number of moles of the reactant metal salt(s) of the (phosph/sulf)ated saccharide(s). Typically, the excess resides within range of about from a fivefold to a twelvefold molar excess of the organic acid compared to the reactant metal salt(s). Preferably, the excess resides within a range about from a sevenfold to a tenfold molar excess of the organic acid thus compared. Most preferably, the excess is an about 8.7 molar equivalent excess of trifluoroacetic acid.

Reaction media are typically aqueous, although other suitable media may be employed with water or apart therefrom to include, for example, methanol, ethanol, and so forth and the like. Water itself is advantageously employed in the preferred practice of this invention.

The reactant metal salt is generally dispersed at a suitable concentration in the reaction medium chosen. Initial concentrations of the reactant metal salt therein include those selected from the range about from 1 molar (M) to 0.0001M (0.1 mM). In a preferred practice of this invention, reactant metal salt concentrations are in general initially about from 1 to 5 mM.

The water soluble organic acid is typically added to the dispersed reactant metal salt. However, this is not required.

The contact of the water soluble acid with the reactant metal salt is carried out at a suitable temperature. Suitable temperatures include those selected from about 0° to 45 degrees C. Advantageously, the temperature at this contact is about from 15° to 30 degrees C., and preferably ambient room temperature.

Generally, the components are mixed at this step of the process. Duration of the step involving the contact of the water soluble organic acid and the reactant metal salt can be from several seconds to several hours or more. Typically, this step is carried out for about from one to ten minutes.

At this point, hydrogen (phosph/sulf)ated saccharides can be generally prepared. It is preferred in the practice of this invention to continue taking the step(s) necessary to prepare the desired bismuth (phosph/sulf)ated saccharides directly and without separation of any hydrogen (phosph/sulf)ated saccharides.

To carry on to prepare the bismuth (phosph/sulf)ated saccharide, the reaction mixture, which contains residues or reaction products of the metal salt of the (phosph/sulf)ated saccharide contacted with the water soluble organic acid employed and which typically contains at least some hydrogen (phosph/sulf)ated saccharide, itself or being prepared in situ, is contacted with the bismuth substance. Typically, the bismuth substance is a solid, and it may advantageously be stirred into the dispersion or solution of the reaction mixture. Alternatively, for example, the bismuth substance may be slurried in water as a sample of fine particles, with the typically aqueous dispersion or solution of the reaction mixture as aforesaid being added thereto. Amounts of the bismuth substance may advantageously be in a slight stoichiometric molar equivalent deficeincy in comparison to the initial amount of phosphorylated or sulfated moiety equivalents of the reactant metal salt, to include, for instance, amounts about from 95 to 99.9 percent of theory, and for example, amounts about 99.4 percent of theory. However, amounts of bismuth substance up to about 105 percent of theory may be employed.

A suitable temperature is employed for this further step as well. Suitable temperatures include those selected about from 0° to 45 degrees C. Advantageously, the temperature at this contact is about from 15° to 30 degrees C., and preferably ambient room temperature.

Generally, the components are mixed at this step of the process. Duration of the step involving contact with the bismuth substance can be about from several minutes to a score (20) hours or more. Typically, this step is carried out for about from half of an hour to about two hours.

Upon completion of the desired progress of reaction, product bismuth (phosph/sulf)ated saccharide is generally separated from other components included in the remaining reaction mixture. This can be accomplished by known methodology. The recovery of the product advantageously can be carried out by suction filtration and washing. The washing may generally be with such liquids as, for example, water, methanol and/or acetone, and so forth and the like. The product can be slurried in methanol and/or acetone and suction filtered therefrom if desired.

The product can be dried after its collection. Advantageously, temperatures of the drying are moderate, and preferably the drying is carried out at ambient temperature under vacuum. Heating of the product, and particularly the bismuth product, to dry it should be avoided because such heating, as in air at temperatures much above usual ambient temperatures, for example, 45 degrees C. or more, may cause its decomposition. Accordingly, the product is advantageously stored under refrigeration, for example, in a refrigerator or freezer. Generally, cautionary protection from exposure to actinic radiation may be provided as with, for example, an amber or opaque glass bottle.

Yields of the product can be exceedingly high, substantially quantitative. Thus, yields of at least about 95 percent of theory, to include yields of about from 98 to 100 percent of theory, are possible by the practice of this invention.

Purity of the product, particularly without additional purifications, can be good. Thus, for example, purity of the bismuth (phosph/sulf)ated saccharide product so obtained can be at least about about 75 percent by weight. However, such co-present products do not materially affect the pharmaceutical value of the bismuth (phosph/sulf)ated saccharide products.

The following examples further illustrate this invention. Parts and percentages therein are by weight unless specified otherwise.

EXAMPLE 1

To a solution of potassium sucrose octasulfate (4.58 g, 3.56 mmol) in water (150 mL) was added trifluoroacetic acid (3.24 g, 28.5 mmol, 8 molar equivalents). The solution was stirred for four minutes and then poured onto a slurry of bismuth hydroxide (7.35 g, 28.3 mmol, 7.95 molar equivalents) in water (50 mL). The reaction was stirred at room temperature for one hour. The resulting solid was collected by suction filtration, washed with water and acetone, and dried under vacuum at ambient temperature. Obtained was complex salt of bismuth hydroxide sucrose octasulfate, i.e., so-called bismuth hydroxide sucrose octasulfate (10.28 g, 99 percent), as a white solid.

Elemental analysis, calculated for $C_{12} H_{30} O_{51} Bi_8 S_8$: C, 4.94; H, 1.04; S, 8.79; Bi; 57.28; K, 0.00; F, 0.00. Found: C, 5.43, 5.30; H, 1.04, 1.00; S, 8.91, 8.70; Bi, 54.83, 55.10; K, 1.06, 1.13; F, 0.052, 0.057.

Karl Fischer water analysis: 5.71, 5.79 percent.

High pressure liquid chromatography (HPLC) analysis: Heptasulfate/octasulfate ratio: 0.057; 29.4 percent sucrose octasulfate residue moiety in the product.

EXAMPLE 2

To a solution of potassium sucrose octasulfate (4.58 g, 3.56 mmol) in water (150) mL) was added trifluoroacetic acid (3.41 g, 29.9 mmol, 8.4 molar equivalents). The solution was stirred for four minutes and then poured onto a slurry of bismuth hydroxide (7.35 g, 28.3 mmol, 7.95 molar equivalents) in water (50 mL). The reaction was stirred at room temperature for 1.5 hours. The resulting solid was collected by suction filtration, washed with water and acetone, and dried under vacuum at ambient temperature. Obtained was bismuth hydroxide sucrose octasulfate (10.24 g, 99 percent) as a white solid.

Elemental analysis, calculated for $C_{12} H_{30} O_{51} Bi_8 S_8$: C, 4.94; H, 1.04; S, 8.79; Bi, 57.28; K, 0.00; F, 0.00. Found: C, 5.18, 5.13; H, 1.01, 1.00; S, 8.55, 8.78; Bi, 54.37, 54.25; K, 0.89, 0.88; F, 0.011, 0.017.

Karl Fischer water analysis: 5.24, 5.29 percent.

HPLC analysis: Heptasulfate/octasulfate ratio: 0.03; 29.4 percent sucrose octasulfate.

EXAMPLE 3

To a solution of potassium sucrose octasulfate (11.0 g, 8.54 mmol) in water (250 mL) was added trifluoroacetic acid (8.47 g, 74.3 mmol, 8.7 molar equivalents). The solution was stirred for four minutes and then poured onto a slurry of bismuth hydroxide (17.66 g, 67.9 mmol, 7.95 molar equivalents) in water (100 mL). The reaction was stirred at room temperature for two hours. The resulting solid was collected by suction filtration, washed with water and acetone, and dried under vacuum at ambient temperature. Obtained was bismuth hydroxide sucrose octasulfate (24.94 g, 100 percent) as a white solid.

Elemental analysis, calculated for $C_{12} H_{30} O_{51} Bi_8 S_8$: C, 4.94; H, 1.04; S, 8.79; Bi, 57.28; K, 0.00; F, 0.00. Found: C, 4.94, 4.89; H, 1.33, 1.35; S, 8.90, 8.84; Bi, 53.61, 53.04; K, 0.82, 0.81; F, 0.0027, 0.0023.

Karl Fischher water analysis: 6.32, 6.43 percent.

HPLC analysis: Heptasulfate/octasulfate ratio: 0.014; 29 percent sucrose octasulfate.

EXAMPLE 4

To a solution of potassium sucrose octasulfate (9.17 g, 7.12 mmol) in water (250 mL) was added trifluoroacetic acid (7.31 g, 64.1 mmol, 9.0 molar equivalents). The solution was stirred for four minutes and then poured onto a slurry of bismuth hydroxide (14.72 g, 56.6 mmol, 7.95 molar equivalents) in water (100 mL). The reaction was stirred at room temperature for 1.5 hours. The resulting solid was collected by suction filtration, washed with water and acetone, and dried under vacuum at ambient temperature. Obtained was bismuth hydroxide sucrose octasulfate (20.68 g, 99 percent) as a white solid.

Elemental analysis, calculated for $C_{12} H_{34} O_{51} S_8 Bi_8$: C, 4.94; H, 1.04f S, 8.79; Bi, 57.28; K, 0.00; F, 0.00. Found: C, 5.23, 5.04; H, 1.05, 1.16; S, 8.78, 8.32; Bi, 54.04, 53.74; K, 0.44, 0.40; F, 0.055, 0.049.

Karl Fischer water analysis: 5.31, 5.63 percent.

HPLC analysis: Heptasulfate/octasulfate ratio: 0.029; 28.9 percent sucrose octasulfate.

EXAMPLE 5

To a solution of potassium sucrose octasulfate (4.58 g, 3.56 mmol) in water (150 mL) was added 4-methylbenzenesulfonic acid monohydrate (5.41 g, 28.5 mmol, 8 molar equivalents). The solution was stirred for four minutes and poured onto a slurry of bismuth hydroxide (7.35 g, 28.3 mmol, 7.95 molar equivalents) in water (50 mL). The reaction was stirred at room temperature for 1.5 hours. The resulting solid was collected by suction filtration, washed with water and acetone, and dried under vaccum at ambient temperature. Obtained was bismuth hydroxide sucrose octasulfate (10.30 g, 99 percent) as a white solid.

Elemental analysis, calculated for $C_{12} H_{30} O_{51} Bi_8 S_8$: C, 4.94; H, 1.04; S, 8.79; Bi, 57.28; K, 0.00. Found: C, 5.11, 5.16; H, 1.07, 1.22; S, 8.92, 8.72; Bi, 55.15, 53.56; K, 0.96, 0.97.

Karl Fischer water analysis: 5.51, 5.48 percent.

HPLC analysis: Heptasulfate/octasulfate ratio: 0.038; 26.7 percent sucrose octasulfate.

EXAMPLE 6

To a solution of potassium sucrose octasulfate (11.0 g, 8.54 mmol) in water (250 mL) was added 4-methylbenzenesulfonic acid monohydrate (13.81 g, 72.6 mmol, 8.5 molar equivalents). The solution was stirred for five minutes and then poured onto a slurry of bismuth hydroxide (17.66 g, 67.9 mmol, 7.95 molar equivalents) in water (150 mL). The reaction was stirred at room temperature for 1.5 hours. The resulting solid was collected by suction filtration, washed with water and acetone, and dried under vacuum at ambient temperature. Obtained was bismuth hydroxide sucrose octasulfate (24.90 g, 100 percent) as a white solid.

Elemental analysis, calculated for $C_{12} H_{30} O_{51} Bi_8 S_8$: C, 4.94f H, 1.04; S, 8.79; Bi, 57.28; K, 0.00. Found: C, 5.38, 5.25; H, 1.22, 1.23; S, 8.32, 8.86; Bi, 53.43, 52.89; K, 1.11, 1.14.

Karl Fischer water analysis: 6.83, 6.91 percent.

HPLC analysis: Heptasulfate/octasulfate ratio: 0.045; 27 percent sucrose octasulfate.

EXAMPLE 7

To a solution of potassium sucrose octasulfate (4.58 g, 3.56 mmol) in water (150 mL) was added trichloroacetic acid (4.71 g, 28.8 mmol, 8.1 molar equivalents). The solution was stirred for four minutes and then poured onto a slurry of bismuth hydroxide (7.35 g, 28.3 mmol, 7.95 molar equivalents) in water (50 mL). The reaction was stirred at room temperature for 1.5 hours. The resulting solid was collected by suction filtration, washed with water and acetone, and dried under vacuum at ambient temperature. Obtained was bismuth hydroxide sucrose octasulfate (10.25 g, 99 percent) as a white solid.

Elemental analysis, calculated for C12 H30 O51 Bi8 S8: C, 4.94; H, 1.04; S, 8.79; Bi, 57.28; K, 0.00; Cl, 0.00. Found: C, 5.65, 5.32; H, 1.07, 1.22; S, 8.59, 8.91; Bi, 53.79, 54.05; K, 0.82, 0.87; Cl, 0.028, 0.029.

Karl Fischer water analysis: 6.43, 6.38 percent.

HPLC analysis: Heptasulfate/octasulfate ratio: 0.038; 28.5 percent sucrose octasulfate.

CONCLUSION

The present invention is thus provided. Various adaptations and modifications can be effected by those skilled in the art within the spirit of this invention, the scope of which is particularly pointed out by the following distinctly claimed subject matter.

What is claimed is:

1. A process for preparing a hydrogen (phosph/sulf)ated saccharide comprising steps of, first, contacting a component of a metal salt of a (phosph/sulf)ated saccharide with a component of a water soluble organic acid having a pKa less than the pKa of the hydrogen (phosph/sulf)ated saccharide to be prepared, and second, maintaining contact of said components in mixture provided by said first step, under conditions such that the hydrogen (phosph/sulf)ated saccharide is prepared.

2. The process of claim 1 wherein the hydrogen (phosph/sulf)ated saccharide is sucrose octasulfate; said metal salt is potassium sucrose octasulfate; said water soluble organic acid is selected from the group consisting of trichloroacetic acid, trifluoroacetic acid and 4-methylbenzesulfonic acid; said water soluble organic acid is employed in a molar excess about from sevenfold to tenfold of the potassium sucrose octasulfate; water is employed as a diluent, and temperatures of the process are about from 0° to 45 degrees C.

3. A process for preparing a bismuth (phosph/sulf)ated saccharide comprising steps of contacting, first, a component of a metal salt of a (phosph/sulf)ated saccharide with a component of a water soluble organic acid having a pKa less than the pKa of a hydrogen (phosph/sulf)ated saccharide corresponding to the bismuth (phosph/sulf)ated saccharide to be prepared, second, the product of said first step with a component of a bismuth substance, and third, maintaining contact of said components in mixture provided by said first and second steps, under conditions such that the bismuth (phosph/sulf)ated saccharide is prepared.

4. The process of claim 3, wherein said metal salt is an alkali metal salt of a (phosph/sulf)ated saccharide; said water soluble acid is selected from the group consisting of carboxylic acids, and sulfonic acids, and said first, and second and third steps are carried out in an aqueous diluent.

5. The process of claim 4, wherein said water soluble acid is employed in an amount about from slightly less than stoichiometric to a moderate excess of equivalents of any hydroxylated, phosphorylated and sulfonated moiety residues present in saccharide residue of said metal salt.

6. The process of claim 5, wherein temperatures of said first, and second and third steps are about from 0° to 45 degrees C.

7. The process of claim 6, wherein (phosph/sulf)ated saccharide moieties are sulfonated, and the bismuth substance is bismuth hydroxide.

8. The process of claim 7, wherein said metal salt is potassium sucrose octasulfate; said water soluble organic acid is selected from the group consisting of trichloroacetic acid, trifluoroacetic acid and 4-methylbenzenesulfonic acid, and is employed in an amount about from seven to ten times as many moles as moles of said metal salt; temperatures of said first, and second and third steps are about from 15° to 30 degrees C., and a complex salt of bismuth hydroxide sucrose octasulfate is prepared in a yield of at least about 99 percent of theory at a purity of at least about 70 percent by weight.

9. A process for preparing a complex salt of bismuth hydroxide sucrose octasulfate comprising contacting potassium sucrose octasulfate with about from eight to nine times as many moles of an organic acid selected from the group consisting of trichloroacetic acid, trifluoroacetic acid and 4-methylbenzenesulfonic acid, as there are moles of the potassium sucrose octasulfate, in an aqueous diluent at a temperature about from 0° to 45 degrees C., then contacting the foregoing mixture with an aqueous mixture with about from 90 to 99 percent as many moles of bismuth hydroxide as there are moles of the potassium sucrose octasulfate, at a temperature about from 0° to 45 degrees C., then separating complex salt of bismuth hydroxide sucrose octasulfate from aqueous reaction mixture.

10. The process of claim 9, wherein the organic acid is trifluoroacetic acid.

* * * * *